United States Patent [19]

Hartmann

[11] Patent Number: 4,870,710
[45] Date of Patent: Oct. 3, 1989

[54] BODY-LIQUID COLLECTING AND MATTRESS PROTECTING APPARATUS

[76] Inventor: Richard Hartmann, Box 91, New Baltimore, N.Y. 12124

[21] Appl. No.: 318,557

[22] Filed: Mar. 3, 1989

[51] Int. Cl.[4] .............................................. A61G 7/02
[52] U.S. Cl. ............................................ 5/90; 5/484; 5/501; 4/455
[58] Field of Search .................. 4/144.1–144.3, 4/450, 451, 455, 456; 5/90, 463, 484, 487, 501, 502; 604/322

[56] References Cited

U.S. PATENT DOCUMENTS

| | | | |
|---|---|---|---|
| 2,567,830 | 9/1951 | Timian | 4/455 |
| 2,614,273 | 10/1952 | Yancofski | 5/90 |
| 3,757,356 | 9/1973 | Freeman | 5/463 |
| 3,889,302 | 6/1975 | Ketterer et al. | 5/484 X |
| 4,747,166 | 5/1988 | Kuntz | 4/456 X |

Primary Examiner—Michael F. Trettel
Attorney, Agent, or Firm—Charles J. Brown

[57] ABSTRACT

Apparatus for protecting a mattress from body-liquids and collecting the body-liquids which includes a flexible liquid-impervious laminated mattress pad within the layers of which is a tube accessed from the upper surface of the pad through holes and also continuous suction means for drawing off through the holes and tube any body liquids deposited on the upper surface of the pad.

13 Claims, 2 Drawing Sheets

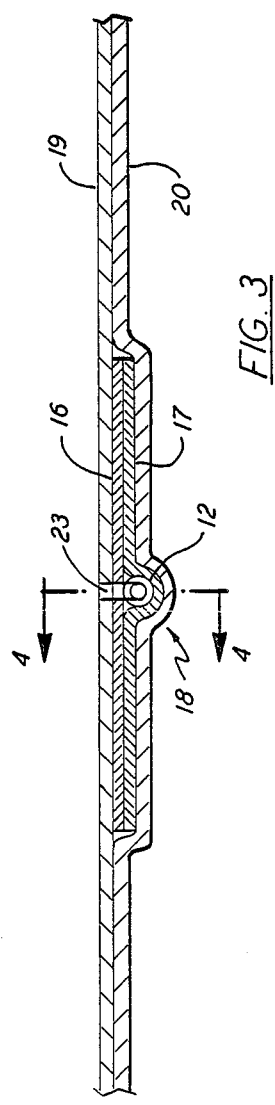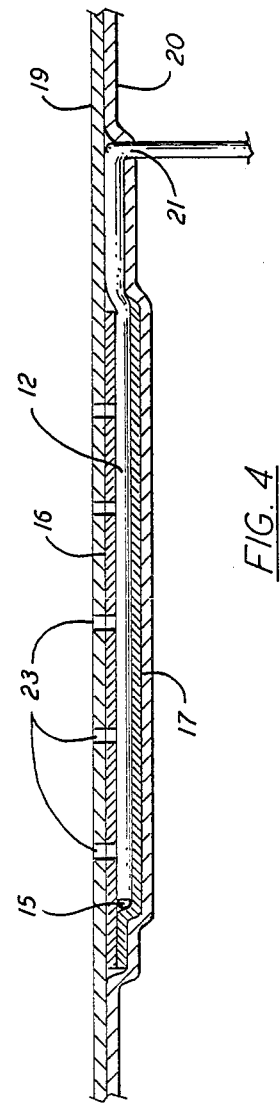

BODY-LIQUID COLLECTING AND MATTRESS PROTECTING APPARATUS

BACKGROUND OF THE INVENTION

For incontinent bedridden persons liquid-impervious pads are generally used over matresses and sheets but it is accepted that substantial accumulations of body liquids may not be contained by conventional pads. Not only is bedding then soiled but accumulations in contact with the skin for any prolonged period pose grave danger of irritation and even ulceration.

It is important, therefore, that discharged body-liquids be collected promptly and removed from contact with the incontinent person. To achieve this without repeated changes of bedding various forms of apparatus have been proposed to collect the body liquids and draw them off by suction from beneath the patient. Perhaps the most relevant of these prior designs is that described in U.S. Pat. No. 3,757,356 in which a shallow expansive pan-like structure overlayed by a perforated cover is connected by a tube to a suction pump. A disadvantage of that design is that it is sufficiently thick to require its own surrounding foam pad of equivalent thickness to present to the patient an even and continuous mattress surface. In U.S. Pat. No. 3,889,302 a somewhat similar pan-like structure is disclosed but again it is relatively thick and must be almost as extensive as the mattress itself to be comfortable to the patient.

It is a principal object of the present invention to provide a laminated mattress pad for use with body-liquid collecting and mattress protecting apparatus which is as thin as possible so that it can lie directly on top of the mattress and sheets without being a discomfort to the patient.

SUMMARY OF THE INVENTION

The invention provides a flexible liquid-impervious laminated mattress pad for use with body-liquid collecting and mattress protecting apparatus. The pad includes an extended central flexible tube sealed at one end. Upper and lower liquid-impervious inner sheets are joined together and enclose that top tube end portion which is sealed. Upper and lower liquid-impervious outer sheets are joined to and enclose the respective inner sheets and a portion of the tube not enclosed within the inner sheets. The lower outer sheet defines an aperture through which the remainder of the tube extends. A plurality of aligned body-liquid collecting holes are provided through the upper outer and upper inner sheets and the wall of the tube end portion is enclosed by the inner sheets.

In a preferred form the laminated mattress pad is combined with suctioning means for applying a vacuum through the tube and holes to draw off and collect any body liquid deposited on the upper outer sheet of the mattress pad. It is also preferred that the upper inner sheet be disposed substantially straight across the tube end portion and the lower inner sheet is then fitted over and around that tube end portion. The upper and lower inner sheets are preferably matched in size and shape and the upper and lower outer sheets are similarly matched in size and shape and are larger than the inner sheets. The upper and lower inner sheets may be joined together by a substantially continuous layer of adhesive and the upper and lower outer sheets may be joined to one another and to the respective upper and lower inner sheets by respective substantially continuous layers of adhesive. The suctioning means may include a sealed container with which the tube communicates, a pneumatic line also communicating with the container, a continuous suctioning pump operably connected to the pneumatic line and dehydrator means in the pneumatic line between the container and the suction pump.

DESCRIPTION OF THE DRAWINGS

FIG. 3 is an enlarged fragmentary section taken along the line 3—3 of FIG. 1; and FIG. 4 is an enlarged fragmentary section taken along the line 4—4 of FIG. 3.

DESCRIPTION OF THE PREFERRED EMBODIMENT

Figure 1:
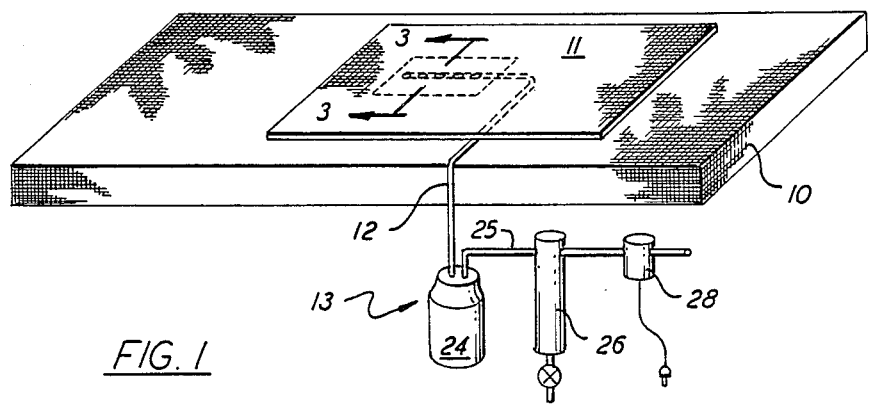
FIG. 1 is a pictorial view in somewhat schematic form, showing the laminated mattress pad of the invention on a mattress with the associated suctioning means.

A mattress 10 is shown in FIG. 1, the head end of which would be to the right in the drawing. It is to be understood that the term "mattress" as used herein is to include not only the mattress itself but also any other conventional pads, sheets or the like constituting the bedding upon which the patient lies and which require protection. On the upper surface of the mattress 10 is the flexible liquid-impervious laminated mattress pad 11 of the invention which may be approximately four feet in length and three feet in width. It is of course centered longitudinally on the mattress and placed somewhat closer to the head end rather than the foot end. As described below a flexible plastic tube 12, perhaps of three-eighth inch diameter, extends from the pad to suctioning apparatus 13 described below.

Figure 2:
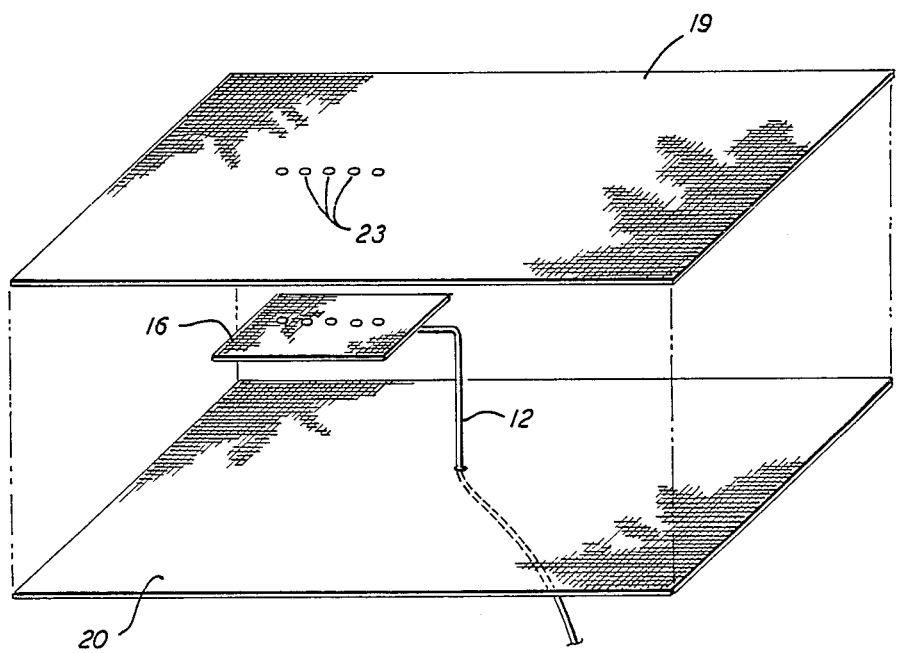
FIG. 2 is an enlarged pictorial exploded view of the mattress pad of the invention showing the various upper and lower sheets which comprise its laminations and the central tube.

Referring now to FIGS. 2 to 4, the tube 12 comprises the central element of the pad 11 and it is sealed by any form of closure plug 15 at one end. Matching rectangular liquid-impervious upper and lower inner sheets 16 and 17 are joined by a substantially continuous layer of adhesive such as contact cement so as to enclose that end of the tube 12 which is sealed. The upper and lower inner sheets 16 and 17 may be of Dacron (a trademark for synthetic polyester textile fabric) sailcloth or the like of rectangular shape perhaps twelve inches in length by eight inches in width. As shown in FIG. 3 the upper inner sheet 16 is disposed substantially straight across or tangentially to the enclosed end portion of the tube 12 while the lower inner sheet 17 is fitted over and around that tube end portion. As a consequence a bulge 18 in the pad formed by the enclosed tube is directed downwardly and not upwardly which would be a source of discomfort to the patient.

The pad also includes matching rectangularly upper and lower liquid-impervious outer sheets 19 and 20 which have a length of perhaps four feet and a width of perhaps three feet. They are joined together and to the respective upper and lower inner sheets 16 and 17 by respective substantially continuous layers of adhesive such as contact cement. The outer sheets 19 and 20 may be of the same flexible material so that of the inner sheets 16 and 17. They enclose not only the inner sheets but also a portion of the tube 12 which is not enclosed within the inner sheets, as shown in FIG. 4. The lower outer sheet defines an aperture 12 through which the remainder of the tube 12 extends.

In the sequence of assembly the inner upper and lower sheets 16 and 17 are first laminated together about the end portion of the tube 12 and the tube 12 is then thrust through the aperture 21 of the lower outer sheet 20. The upper and lower outer sheets 19 and 20 are then laminated together and to the inner sheets 16 and 17 and the tube 12 by continuous layers of adhesive. The next step is to punch or drill a plurality of aligned body-liquid collecting holes 23 through the upper outer and upper inner sheets and the wall of the tube end portion enclosed by the inner sheets, as shown particularly in FIGS. 3 and 4. In this example five such holes are formed and, as is apparent from FIG. 1, they will be located along the centerline of the mattress approximately midway between its head and foot ends.

The suctioning means 13 for applying a vacuum through the tube 12 and the holes 23 to draw off and collect body-liquids deposited on the upper outer sheet 19 of the mattress pad 11 are shown schematically in FIG. 1. They comprise a sealed container 24 with which the tube 12 communicates and a pneumatic line 25 which communicates with the container 24 and leads to a dehydrator 26 equipped with a conventional bleeder valve 27. Both the dehydrator and the pneumatic line extend to an electrically powered continuous suction pump 28 such as is used in fish tanks. A U-bend, not shown, may be provided in the pneumatic line 25 between the dehydrator 26 and the pump 28 to collect whatever small amounts of moisture may be suctioned past the dehydrator 26.

The laminated pad of the invention and its associated suction equipment are very inexpensive and of simple construction. The pad may be used not only on conventional mattresses but also on either airpads or sand beds. The pad does not require that any holes or apertures be made in the mattress or its sheets and does not interfere with changes of elevation of the head or foot of the bed. The entire apparatus can be rolled up for compact storage.

The scope of the invention is to be determined by the following claims rather than the preferred embodiment described above.

I claim:

1. For use with body-liquid collecting and mattress protecting apparatus, a flexible liquid-impervious laminated mattress pad comprising
   (a) an extended central flexible tube sealed at one end,
   (b) upper and lower liquid-impervious inner sheets joined together and enclosing that tube end portion which is sealed,
   (c) upper and lower liquid-impervious outer sheets joined together and enclosing the respective inner sheets and a portion of the tube not enclosed within the inner sheets,
   (d) the lower outer sheet defining an aperture through which the remainder of the tube extends, and
   (e) a plurality of aligned body-liquid collecting holes through the upper outer and upper inner sheets and the wall of the tube end portion enclosed by the inner sheets.

2. A laminated mattress pad according to claim 1 wherein the upper inner sheet is disposed substantially straight across the enclosed tube end portion and the lower inner sheet is fitted over and around said tube end portion.

3. A laminated mattress pad according to claim 1 wherein the upper and lower inner sheets match in size and shape and the upper and lower outer sheets match in size and shape and are larger than the inner sheets.

4. A laminated mattress pad according to claim 1 wherein the upper and lower inner sheets are joined together by a substantially continuous layer of adhesive and the upper and lower outer sheets are joined together and to the respective upper and lower inner sheets by respective substantially continuous layers of adhesive.

5. Body-liquid collecting and mattress protecting apparatus comprising
   (a) a flexible liquid-impervious laminated mattress pad comprising
      i. an extended central flexible tube sealed at one end,
      ii. upper and lower liquid-impervious inner sheets joined together and enclosed that tube end portion which is sealed,
      iii. upper and lower liquid-impervious outer sheets joined together and enclosing the respective inner sheets and a portion of the tube not enclosed within the inner sheets,
      iv. the lower outer sheet defining an aperture through which the remainder of the tube extends, and
      v. a plurality of aligned body-liquid collecting holes through the upper outer and upper inner sheets and the wall of the tube end portion enclosed by the inner sheets; and
   (b) suctioning means for applying a vacuum through said tube and holes to draw off and collect any body-liquids deposited on the upper outer sheet of the mattress pad.

6. Body-liquid collecting and mattress protecting apparatus according to claim 5 wherein the upper inner sheet is disposed substantially straight across the enclosed tube end portion and the lower inner sheet is fitted over and around said tube end portion.

7. Body-liquid collecting and mattress protecting apparatus according to claim 5 wherein the upper and lower inner sheets match in size and shape and the upper and lower outer sheets match in size and shape and are larger than the inner sheets.

8. Body-liquid collecting and mattress portecting apparatus according to claim 7 wherein the suctioning means includes a sealed container with which said tube communicates, a pneumatic line also communicating with said container and a continuous suction pump operatively connected to said pneumatic line.

9. Body-liquid collecting and mattress protecting apparatus according to claim 8 wherein dehydrator means are located in the pneumatic line between the container and the suction pump.

10. Body-liquid collecting and mattress protecting apparatus according to claim 5 wherein the upper and lower inner sheets are joined together by a substantially continuous layer of adhesive and the upper and lower outer sheets are joined to one another and to the respective upper and lower inner sheets by respective substantially continuous layers of adhesive.

11. Body-liquid collecting and mattress protecting apparatus according to claim 5 wherein the suctioning means includes a sealed container with which said tube communicates, a pneumatic line also communicating with said container and a continuous suction pump operatively connected to said pneumatic line.

12. Body-liquid collecting and mattress protecting apparatus according to claim 11 wherein dehydrator means are located in the pneumatic line between the container and the suction pump.

13. Body-liquid collecting and mattress protecting apparatus comprising
(a) A flexible liquid-impervious laminated mattress pad comprising
  i. an extended central flexible tube sealed at one end,
  ii. matching rectangular upper and lower liquid-impervious inner sheets joined by a substantially continuous layer of adhesive and enclosing that tube end portion which is sealed,
  iii. the upper inner sheet being disposed substantially straight across the enclosed tube end portion and the lower inner sheet being fitted over and around said tube end portion,
  iv. matching rectangular upper and lower liquidimpervious outer sheets of a length and width greater than the inner sheets joined together and to the respective upper and lower inner sheets by respective substantially continuous layers of adhesive and enclosing the inner sheets and a portion of the tube not enclosed within the ineer sheets,
  iv. the lower outer sheet defining an aperture through which the remainder of the tube extends, and
  v. a plurality of aligned body-liquid collecting holes through the upper outer and upper inner sheets and the wall of the tube end portion enclosed by the inner sheets; and
(b) suctioning means for applying a vacuum through said tube and holes to draw off and collect any body-liquids deposited on the upper outer sheet of the mattress pad.

* * * * *